United States Patent [19]

Ayer et al.

[11] Patent Number: 4,847,093
[45] Date of Patent: Jul. 11, 1989

[54] DOSAGE FORM WITH MEANS FOR GOVERNING RATE OF GAS FORMATION

[75] Inventors: Atul D. Ayer, Mountain View; Patrick S. L. Wong, Hayward, both of Calif.

[73] Assignee: ALZA Corporation, Palo Alto, Calif.

[21] Appl. No.: 668,761

[22] Filed: Jun. 19, 1986

[51] Int. Cl.$^4$ .......................... A61K 9/44; A61K 9/46
[52] U.S. Cl. ...................................... 424/473; 424/44; 514/165
[58] Field of Search .................... 424/44, 473

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,036,228 | 7/1977 | Theeuwes | 424/473 |
| 4,200,098 | 4/1980 | Ayer et al. | 128/260 |
| 4,203,439 | 5/1980 | Theeuwes | 424/473 |
| 4,235,236 | 11/1980 | Theeuwes | 424/473 |
| 4,265,874 | 5/1981 | Bonsen et al. | 424/44 |
| 4,344,929 | 8/1982 | Bonsen et al. | 424/44 |

*Primary Examiner*—Shep K. Rose
*Attorney, Agent, or Firm*—Paul L. Sabatine; Edward L. Mandell; Steven F. Stone

[57] ABSTRACT

An osmotic device is disclosed comprising a release rate controlling wall that surrounds a carbon dioxide generating compound.

7 Claims, 3 Drawing Sheets

DOSAGE FORM WITH MEANS FOR GOVERNING RATE OF GAS FORMATION

CROSS-REFERENCE TO RELATED COPENDING APPLICATION

This application is copending with an application U.S. Ser. No. 06/874,961 filed June 16, 1986 and issued as U.S. Pat. No. 4,755,180 on July 5, 1988.

FIELD OF THE INVENTION

This invention pertains to both a novel and useful dosage form. More particularly, the invention concerns an improved dosage form that uses gas for dispensing a beneficial drug, the improvement comprising means for governing the rate of gas formation in the dosage form.

BACKGROUND OF THE INVENTION

Dosage forms manufactured in the shape of an osmotic device for delivering a drug to a biological environment of use are known to the dispensing art in U.S. Pat. Nos. 3,845,770 and 3,916,899, both issued to inventors Theeuwes and Higuchi. The dosage form disclosed in these patents comprises a semipermeable wall that surrounds a compartment containing a drug. There is a passageway in the wall for delivering the drug from the dosage form. The dosage form releases the drug by fluid being imbibed through the semipermeable wall into the compartment at a rate determined by the permeability of the wall and the osmotic pressure gradient across the wall. This action produces a solution containing soluble drug that is dispensed through the passageway over time.

The dosage form described in the above patents is an outstanding invention and represents a pioneer advancement in the delivery art. In U.S. Pat. No. 4,062,228 patentee Theeuwes made an inventive improvement in this dosage form for delivering drugs that are hard to deliver, particularly drugs that are insoluble in aqueous fluids. The invention in this latter patent consists essentially in charging the dosage form with an effervescent couple consisting of an acidic component and a basic component. In operation, when the dosage form is in a fluid environment, the couple imbibes fluid into the system, thereby wetting the couple causing it to reach and produce an effervescent solution. The effervescent solution is dispensed through a passageway from the dosage form. The effervescent couple instantly reacts in the presence of the imbibed fluid and immediately delivers the drug from the dosage form.

The dosage form disclosed in U.S. Pat. No. 4,062,288 presented immediately above represents a major advancement for delivering hard to delivery drugs, but it lacks the means for governing the rate of gas production over a prolonged period of time for correspondingly delivering the drug over a prolonged period of time.

In the light of this discussion, it will be readily appreciated by those skilled in the subject dispensing art that a critical need exists for a means for governing the rate of gas production over time accompanied by delivering the drug over a similar period of time. It will further appreciated by those skilled in the art, that if a novel and useful dosage form is made available for delivering these drugs, such a dosage form would have a positive value and also represents a substantial contribution to the dispensing art.

OBJECTS OF THE INVENTION

Accordingly, in the light of the above presentation, it is an immediate object of this invention to provide a novel and useful dosage form that overcomes the difficulties known to the prior art.

Another object of the present invention is to provide a dosage form comprising means for generating a gas and for simultaneously governing the rate of gas production in the dosage form.

Another object of the present invention is to provide a dosage form for delivering drugs that are difficult to deliver attributed to their poor solubility in aqueous fluid, but can be delivered by the dosage form through its ability to produce a drug delivery gas at a controlled rate over time.

Another object of the present invention is to provide a dosage form manufactured as an osmotic dispensing device, which dosage form comprises means for generating and controlling the rate of gas production useful for delivering a drug as a complete pharmaceutical regimen to a human for a particular time period, the use of which requires intervention only for initation and optional termination of the regimen.

Another object of the invention is to provide a polymeric formulation that surrounds a basic compound that is released by the polymeric formulation for reacting with a acidic compound in a dosage form whereby the compound is delivered from the dosage form over time.

Other objects, features and advantages of the invention will be more apparent to those skilled in the dispensing art from a reading of the detailed description of the specification, taken in conjunction with the drawing figures and the accompanying claims.

BRIEF DESCRIPTION OF THE DRAWING FIGURES

In the drawing figures, which are not drawn to scale, but are set forth to illustrate various embodiments of the invention, the drawing figures are as follows.

In the drawing figure and in the specification, like parts in related figures are identified by like numbers. The terms appearing earlier in the specification, and in the description of the drawing figures, as well as embodiments thereof, are further described elsewhere in the disclosure.

DETAILED DESCRIPTION 0F THE DRAWING FIGURES

Figure 1:
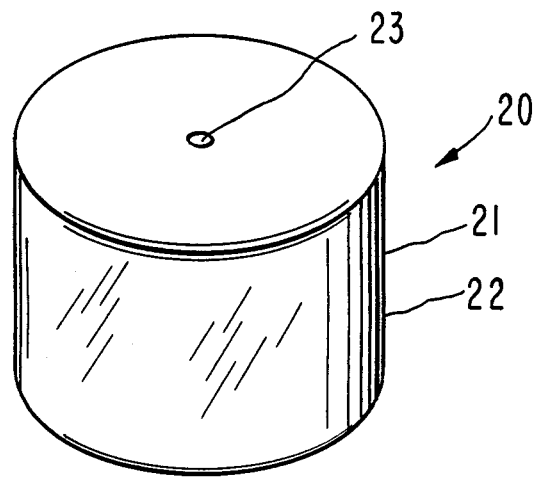
FIG. 1 is a general view of a dosage form provided by the invention, which dosage form is designed and shaped for oral administration of a beneficial drug.

Turning now to the drawing figures in detail, which drawing figures are an example of the dosage form provided by the invention, and which examples are not to be construed as limiting, one example of the dosage form is illustrated in FIG. 1 and designated by the numeral 20. In FIG. 1, dosage form 20 comprises a body member 21 comprising a wall 22 that surrounds and forms an internal compartment, not seen in FIG. 1. Dosage form 20 further comprises at least one exit means 23 for connecting the interior of dosage form 20 with the exterior biological environment of use.

Figure 2:
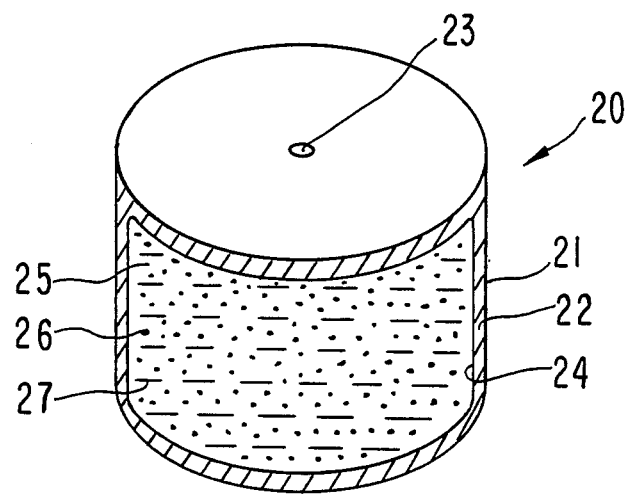
FIG. 2 is a dosage form seen in opened section for illustrating the internal structure of the dosage form; and, FIG. 3 is a dosage form seen in opened section which dosage form comprises a microporous releasing member.

FIG. 2 llustrate dosage form 20 of FIG. 1 comprising body 21, wall 22 and exit means 23. Wall 22 is opened at 24, with wall 22 surrounding and defining an internal compartment 25. Wall 22 of dosage form 20 comprises in at least a part, or totally, a composition that is permeable to the passage of an exterior fluid present in the environment of use, and it is substantially impermeable to the passage of a drug and other ingredients present in compartment 25. Wall 22 comprises a polymeric composition that is inert and maintains its physical and chemical integrity during the dispensing life time of dosage form 20. The phrase, "keeps its physical and chemical integrity" is an art accepted phrase that denotes wall 22 does not lose its structure and it does not change during the dispensing life of dosage 20. Typical materials for forming wall 22 comprise selectively semipermeable polymers known to the art as osmosis and reverse osmosis polymers. These polymeric compositions comprise a member selected from the group consisting of a cellulose ester, cellulose ether, cellulose ester-ether, cellulose acylate, cellulose diacylate, cellulose triacylate, cellulose acetate, cellulose diacetate, and cellulose triacetate. In a presently preferred embodiment wall 22 is a composition comprising cellulose acetate having an acetyl content of 32%, cellulose acylate having an acetyl content of 39.8%, or cellulose acylate having an acetyl content 43.3%.

Internal compartment 25 houses a dispensable drug formulation 26, identified by dots, and a gas generating means 27, identified by dashes. The expression drug formulation 26 as used for the purpose of this invention broadly includes any compound, composition of matter, or mixture thereof, that can be delivered from the device to produce a beneficial and useful therapeutic result. The term "drug" more specifically includes any substance that produces a local or a systemic effect in animals, avians, pisces and reptiles. The term "animals", includes primates, humans, household, sport, and farm animals, such as goats, cattle, horses, dogs, cats, and the like. The drugs that can be delivered by the dosage from of the invention include organic and inorganic drugs.

A more specific groups of drugs suitable for dispensing by dosage form 20 are the acidic anti-inflammatory drugs. The anti-inflammatory drugs are represented by arylcarboxylic acid drugs and enolic acid drugs. Examples of arylcarboxylic acid drugs include alclofenac or 4-allyloxy-3-chlorophenylacetic acid; aspirin or acetylsalicylic acid; fenoprofen or d1-2-(3-phenoxyphenyl) propionic acid, flufenamic acid or 2-)3-benzoylphenyl)propionic acid; ibuprofen or α-methyl-4-(2-methylpropyl)benzene acetic acid; metiazinic acid or 10-methyl-2-phenothiazinylacetic acid; naproxen or d-2-(6'-methoxy- 2'-naphthyl)-methyl-2-phenyl-aminonicotinic acid; tolmetin or 1- methyl-5-p-toluylpyrrole-2-acetic acid; and sulindac or cis-5-fluoro- 2-methyl-1-[p-(methylsulfinyl)-benzylidene]indene-3-acetic acid. Examples of enolic acidic drugs include azapropazone or 3-dimethyl- amino-7-methyl-1,2-(n-propylmalonyl)-1-1-dihydro-1,2,4-benzotriazine; phenylbutazone or 3,5-dioxo-4-n-butyl-1,2-diphenypyrazolidine; prenazone or 4-prenyl-1,2-diphenyl-3-pyrrazolidine-drone; sudoxicam or 4-hydroxy-2-methyl-n-(2-thiazolyl)-2H-1,2-benzothiazine-3-carboxamide-1,2-dioxide and the like. Other antiinflammatory drugs include diclofenac or 2-[2,6-dichlorophenyl)-amino]benzeneacetic acid; and peroxicam or 2H-1,2-benzothiazine-3-carboxamide.

The amount of drug present in dosage form 20 will vary depending on the activity and the amount of drug to be administered to the host. Generally, dosage form 20 will house from 0.5 mg to 1.250 g or more, with individual dosage forms containing for example 5 mg, 25 mg, 50 mg, 100 mg, 125 mg, 200 mg, 250 mg, 500 mg, and the like. The drug can be in dosage form 20 in various forms such as dispersion, granules, powder, pressed powders, and the like. The beneficial drugs, their solubilities, their present doses are known to the drug dispensing art in *Pharmaceutical Sciences* by Remington, 15th Ed., 1975published by the Mack Publishing Co., Easton, Pa; and in *USAN And The USP Dictionary Of Drug Names*, Mary G. Griffiths, Ed., 1985 published by USP Convention Ind., Rockville, Md., 20852.

Figure 3:
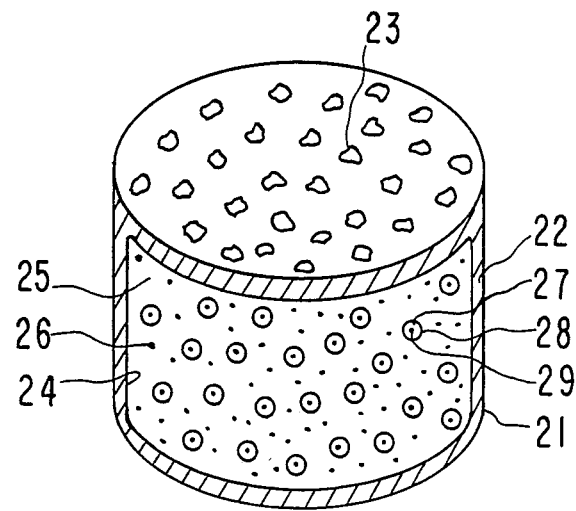

Gas generating means 27 in internal compartment 26 comprises an agent release rate controlling wall that surrounds and confines a solid, basic compound that comprises a carbon dioxide producing moiety. Gas generating means 27 is seen in greater detail in FIG. 3. In FIG. 3, gas generating means 27 comprising agent release rate controlling wall 28 that surrounds carbon dioxide producing compound 29. Examples of release rate controlling materials that can be used for this purpose are a member selected from the group consisting essentially of olefin and vinyl-type polymers; condensation-type polymers; addition-type polymers; organosilicon polymers; and the like. More specifically, polymeric materials that can be used for this purpose include poly(methylmethacrylate); poly(butylmethacrylate); poly(ethylene); ethylene vinylacetate copolymer; poly(dimehtylsiloxane); poly(urethane); cellulosics and the like.

Gas generating member 29 operable for the present purpose includes a member selected from the group consisting of a non-toxic metal carbonate and non-toxic bicarbonate. The compounds are generally known as salts and they embrace alkali metal carbonate and bicarbonates and the alkaline earth carbonates and bicarbonates. The preferred compounds are those soluble in water and effervesce on contact with the acid drug formulation 26. Exemplary basic compounds include ammonium carbonate, lithium carbonate, sodium carbonate, potassium carbonate, lithium bicarbonate, sodium bicarbonate, potassium bicarbonate, ammonium bicarbonate, magnesium carbonate, calcium carbonate, magnesium bicarbonate, and the like. The amount of basic compound housed in compartment 25 and surrounded by wall 28 is about 0.5 mg to 1250 mg, and preferably 25 mg to 500 mg. The compounds and their solubilities are known in *The Handbook of Chemistry and Physics*, 4th Ed., 1968, published by the Chemical Rubber Co., Cleveland, Ohio.

The rate of passage, that is the rate of release of basic compound 29 through release rate controlling wall 28, can be determined by standard procedures. Various techniques such as the transmission method, the sorption method, and the like can be used as measures of permeability. One technique that can be used is to cast or hot press a film of the material to a thickness in the range of 1 to 30 mils. The film is used as a barrier between a rapidly stirred, for example 150 r.p.m., saturated solution of the compound and a rapidly stirred solvent bath, both maintained at constant temperature, usually 37° C. Samples are withdrawn periodically from the solvent bath and analyzed for compound concentration. Then, by plotting compound 29 concentration in the solvent bath versus time, the permeability constant P of the material is determined by Fick's First Law of Diffusion, as follows:

$$\text{Slope of plot} = \frac{Q_1 - Q_2}{t_1 - t_2} = P\frac{AC}{H}$$

wherein $Q_1$ is the cumulative amount of compound 29 in solvent in micrograms at $t_i$; $Q_2$ is the cumulative amount of drug in solvent in micrograms at $t_2$; $t_i$ is the elapsed time to the first sample, i.e. $Q_1$; $t_2$ is the elapsed time to the second sample, i.e. $Q_2$; A is the area of film in cm$^2$; C is the initial concentration of compound 29; and h is the thickness of the film in cm. By determining the slope of the plot, and solving the equation using the known or measured values of A, C, and h, the permeability P constant in cm$^2$/time of the material for a given compound is determined for the purpose of the invention.

The expression "exit means 23" as used herein comprises means and methods suitable for releasing the drug formulation from the compartment. The expression includes at least one passageway, or two passageways with one on each face of dosage form 20. The passageway or orifice passes through wall 22 for communicating with compartment 25. The expression passageway includes aperture, orifice, bore, pore, porous element through which a drug can migrate, a hollow fiber, capillary tube, and the like. The expression includes also a material that erodes or is leached from wall 22 in the fluid environment of use to produce at least one passageway in dosage form 20. Representative materials suitable for forming at least one passageway or a multiplicity of passageways include an erodible poly(glycolic) or poly(lactic) acid member in the wall, a gelatinuous filament, leachable materials such as a removable pore forming polysaccharide, salt or oxide, and the like. A passageway or a plurality of passageways can be formed by leaching a material such as sorbitol from the wall to produce a controlled release passageway. The passageway can be a microporous member as seen in FIG. 3. The microporous passageways comprising the microporous member can be preformed or formed during operation of the dosage form. The passageway can have any shape such as round, elliptical and the like. Passageways are disclosed in U.S. Pat. Nos. 3,916,899; 4,063,064; and 4,088,864. Passageways of controlled dimensions formed by leaching are disclosed in U.S. Pat. No. 4,200,098.

Wall 22 of dosage form 20, and wall 28 surrounding gas generating compound 29, can be formed using an air suspension procedure. The procedure consisting in suspending and tumbling (a) compressed drug 26 and coated compound 29, or (b) compound 29 in a current of air and using a wall forming composition, until in either operation the compressed layer (a) or compound (b) is applied to (a) or (b). The air suspension procedure is well-suited for independently forming the wall in either operation. The air suspension procedure is described in U.S. Pat. No. 2,799,241; in *J. Am. Pharm. Assoc.*, Vol. 48, pp 451 to 459, 1959; and ibid, Vol. 49, pages 82 to 84, 1960. The wall forming composition can be applied with a Wurster ® air suspension coater, or an Aeromatic ® air suspension coater can be used for forming the wall. Other wall-forming techniques such as pan coating can be used for providing the dosage form. In the pan coating system, the wall forming composition are deposited by successive spraying of the composition accompanied by tumbling in a rotating pan. A pan coater is used to produce a thicker wall or lamina. Finally, the wall coated dosage form, or the wall coated compound are dried in a forced air oven at 50° C. for a week, or in a temperature and humidity controlled oven, 50° C. and 50° R.H. for 24 hours. Generally, the wall formed by these techniques have a thickness of 2 to 20 mils with a presently preferred thickness of 4 to 10 mils.

Exemplary solvents for manufacturing the wall include inert organic and organic solvents that do not adversely harm the wall, and the final dosage form. The solvents broadly include a member selected from the group consisting of an alcohol, ketone, ester, ether, aliphatic hydrocarbon, halogenated solvents, cycloaliphatic solvents, aromatic, heterocyclic, aqueous solvents, mixtures thereof and the like.

The dosage form of the invention is manufactured by standard techniques. For example, in one manufacture the beneficial drug and the walled carbon dioxide moiety are blended and pressed into a solid layer. The layer possesses dimensions that correspond to the internal dimensions of the area occupied in the dosage form. Optionally the drug formulation and the walled carbon dioxide member can be blended with a solvent, mixed by conventional methods such as ballmilling, calendering, stirring or rollmilling and then pressed into a preselected shape. The compressed compartment forming mass is then coated with an outer wall. The wall forming composition can be applied by press coating, molding, spraying, dipping or air suspension procedures. The air suspension and air tumbling procedures comprise suspending and tumbling the pressed composition until surrounded by the wall.

In another manufacture, the dosage form is made by the wet granulation technique. In the wet granulation technique the drug is blended with other compartment forming ingredients using an organic cosolvent, such as isopropyl alcbhol-methylene dichloride, 80/20 v/v (volume/volume) as the granulation fluid. The ingredients are passed through a 40 mesh screen and blended in a mixer. Then, the walled carbon dioxide member is added with continual mixing in the blender. The blend is dried for 18 to 24 hours at 42° C. in a forced air oven. Next, a lubricant is added to the dry blend, and the newly formed mixture put into milling jars and mixed on a jar mill for 5 to 15 minutes. The composition is pressed into a layer in a Manesty ® layer press at a maximum load of 2 tons. The pressed mass is fed to a Kilian ® dry Coata press and coated with an exterior wall.

Another manufacturing process that can be used for providing the compartment-forming composition comprises blending a powdered drug and other ingredients in a fluid bed granulation. After the powdered ingredients are dry blended in the granulator, a granulating fluid, for example, polyvinyl pyrrolidone in water, and the walled gas producing member, are added and the granulating fluid sprayed onto the powder and member. The coated powder and member then are dried in the granulator. After drying, a lubricant such as magnesium stearate is added to the granulator. The granules are then pressed in the manner described above.

DESCRIPTION OF EXAMPLES OF THE INVENTION

The following examples are merely illustrative of the present invention and they should not be considered as limiting the scope of the invention in any way, as these examples and other equivalents thereof will become more apparent to those versed in the dispensing art in the light of the present disclosure, the drawing figures and the accompanying claims.

EXAMPLE 1

A dosage form is manufactured for delivering a beneficial drug as follows: first, 500 g of aspirin, 80 to 120 mesh powder, is granulated in an Aeromatic ® fluid bed granulator. The granulating fluid consist of 8 g of hydroxypropyl methylcellulose dissolved in 350 ml of alcohol. The granules are dried in a forced air oven for 4 hrs at 50° C. and passed through a 20 mesh sieve.

Then, 215 g of sodium bicarbonate powder is granulated in the fluid bed granulator. The granulating fluid consists essentially of 8 g of hydroxypropyl methylcellulose dissolved in 200 ml of alcohol. The granules are dried in a forced air oven for 10 hrs at 50° C. and then passed through a 20 mesh sieve.

Next, the granules of aspirin and the granules of sodium bicarbonate are mixed together in a V-blender for 10 minutes, and then transferred to a Manesty ® tablet press hopper. The press is set with a 7/10 inch oval die and punch. The machine presses 770 mg of the ingredients to yield a precompartment forming core containing 500 mg of aspirin.

Next, the following materials are blended together using a methylene chloride and methanol solvent system: cellulose acetate having an acetyl content of 43.5%, 190 g; polyethylene glycol mol. wt 3350, 10 g; methylene chloride 4377 ml; methanol 982 mil. The solution is used for coating the compressed drug mass. The compressed masses are placed in a Hi-Coater ® pan and coated with the wall-forming composition. A 40 mg wall is applied to each dosage form. The active dosage forms are dried in a forced air oven for 2 days at 45° C. to remove the residual solvent. Then, a 25 mil exit port is drilled through the wall for releasing the aspirin from the dosage form.

Figure 4A:
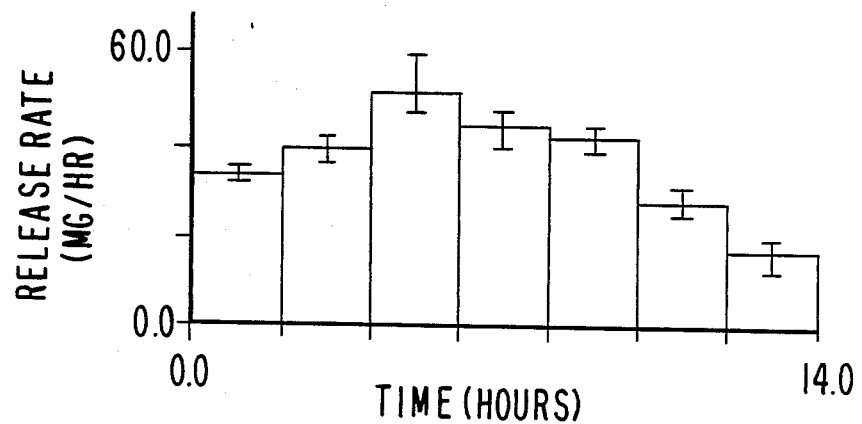
FIGS. 4A and 4B depict the release rate pattern and the cummulative amount released from asprin for the dosage form.
Figure 4B:
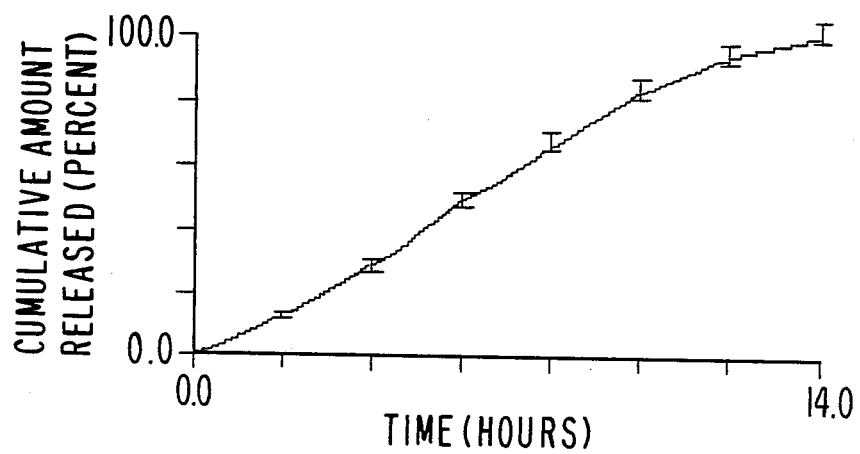

The release of aspirin from the dosage system is measured in artificial gastric fluid for the first four hours and from hours 4 to 14 in artificial intestinal fluid. The release rate for aspirin is plotted in FIGS. 4A and 4B.

EXAMPLE 2

The procedure of Example 1 is followed for manufacturing a dosage form comprising two 6.5 mil (0.17 mm) passageways on two opposite surfaces of the dosage form for dispensing the drug in two directions from the dosage form in the gastrointestinal tract.

EXAMPLE 3

The procedure of Example 1 is repeated with conditions as set for except that in this example the dosage form consists of 120 mg, of pseudoephedrine hydrochloride for up to 12 hour relief of stuffy nose and head cold.

EXAMPLE 4

A dosage form for dispensing indomethacin is prepared as follows: first, 670 g of indomethacin, 30 g of cross-linked polyvinylpyrrolidone and 20 g of polyvinyl-pyrrolidone are mixed in a bowl mixer at a low speed for 30 minutes. Slowly, 300 ml of denatured alcohol is added to the blend while continuing the blending for 10 minutes. The wet granules are passed through a 20 mesh sieve and dried in a forced air oven at 50° C. for 10 hours.

Next, 240 g of sodium bicarbonate powder is granulated in a fluid bed granulator. The granulating fluid consists of 220 ml of alcohol (ethylalcohol) and 20 g of polyvinyl-pyrrolidone. The grannules are dried in a forced air oven at 50° C. for 5 hours.

Next, the granules of indomethacin and the granules of sodium bicarbonate are mixed in a blender with 20 g of magnesium stearate for 20 minutes. The homogeneous blend is then transferred to a Kilian ® tablet press using 5 mm dies and a 20 punch stations. The compressed drug containing mass formed by the press each had a diameter of 5 mm and weight 75 mg. Each individual compressed mass contained 50 mg of indomethacin.

Figure 5A:
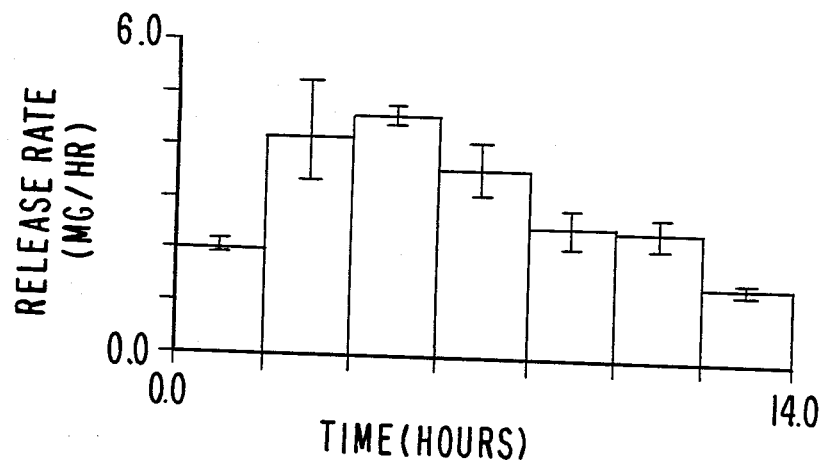
FIGS. 5A and 5B depict the release rate pattern and the cumulative amount released from indomethacin for the dosage form.
Figure 5B:
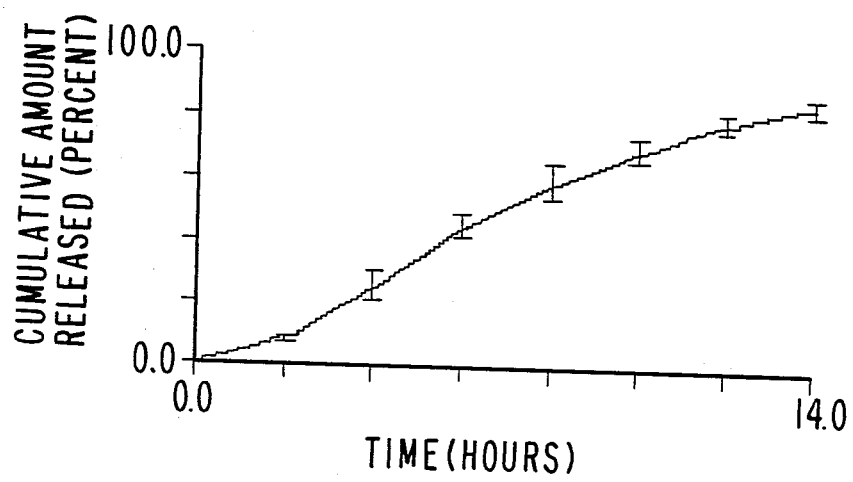

Next the compressed compartment forming members are transferred to an Aeromatic ® coater air-suspension machine. The coating composition consist essentially of cellulose acetate having an acetyl content of 39.8%, and 10% polyethylene glycol having a molecular weight of 3350, dissolved in methylene chloride-methanol cosolvent, 80:20 by wt. The compressed masses are surrounded with an 8 mg semipermeable wall. The dosage forms are dried in an oven at 50° C. for 48 hours to evaporate solvents. A 0.36 mm passageway is drilled through each walled dosage form connecting the exterior of the dosage form with its internal compartment. Accompanying FIGS. 5A and 5B depict the release rate from the dosage form. The release rate during the first four hours is measured in artificial gastric fluid and the release rate in the subsequent 10 hours is measured in artificial intestinal fluid.

EXAMPLE 5

The procedure of Example 4 is followed with the conditions as set forth, except that in this example the passageway consists of copolymeric ethylene-vinyl acetate with sorbitol that is leached from the copolymer to provide at least one passageway formed when the dosage form is in use.

EXAMPLE 6

The procedure of example 4 is repeated except that in this example the beneficial agent in the dosage form is the chlorotheophylline salt of the antihistaminic drug diphenhydramine indicated for the prevention and the treatment of nausea, vomiting and vertigo associated with motion sickness.

In summary, it will be readily appreciated that the present invention contributes to the art an unobvious dosage form manufactured as a drug delivery device possessing wide and practiced applications. While the invention has been described and pointed out in detail and with reference to operative embodiments thereof, it will be appreciated that those skill in the art will appreciate that various changes, modifications, substitutions and omissions can be made without departing from the spirit of the invention. It is intended, therefore, that this invention embrace those equivalents within the scope of the invention disclosed and claimed.

We claim:

1. Dosage form for delivering a beneficial drug formulation to an environment of use, comprising:

(a) a wall comprising at least in part a composition permeable to the passage of fluid and substantially impermeable to the passage of a drug formulation, which wall surrounds and defines:
(b) a compartment;
(c) a dosage amount of a beneficial drug formulation comprising aspirin in the compartment;
(d) means for producng carbon dioxide in the compartment, said means comprising a release rate controlling wall surrounding a pharmaceutically acceptable compound selected from the group consisting of a water soluble carbonate and bicarbonate comprising a carbon dioxide producing group, and which compound when released by the means effervesces on contact with drug formulation comprising aspirin; and,
(e) exit means in the wall of the dosage form that connects compartment with the exterior of the dosage form for delivering the drug formulation from the dosage form.

2. A dosage form for delivering a beneficial drug formulation to a biological environment of use, wherein the dosage form comprises:
(a) a wall comprising at least in part a composition permeable to the passage of fluid present in the biological environment and substantially impermeable to the passage of a drug formulation, which wall surrounds and forms;
(b) a compartment;
(c) a dosage amount of a benefical anti-inflammatory drug comprising an acidic group in the compartment;
(d) means for producing carbon dioxide in the compartment, said means comprising a wall comprising a release rate controlling composition that surrounds a pharmaceutically acceptable compound selected from the group consisting of a water soluble carbonate and bicarbonate, which carbonate and bicarbonate when released by the means effervesce on contact the the anti-inflammatory drug; and,
(e) a passageway in the wall of the dosage form connecting the compartment with the exterior of the dosage form for delivering the drug in a therapeutically effective amount to the environment of use over time.

3. The dosage form for delivering a beneficial drug formulation according to claim 2, wherein the passageway is formed by fluid leaching a leachable compound from the wall when the dosage form is in the biological environment.

4. The dosage form for delivering a beneficial drug formulation according to claim 2, wherein the passageway comprises at least one pore of controlled porosity.

5. The dosage form for delivering a beneficial drug formulation according to claim 2, wherein the passageway comprises a plurality of micropores of controlled porosity.

6. The dosage form for delivering a beneficial drug formulation according to claim 2, wherein the biological environment is the gastrointestinal tract and the dosage form is adapted for oral admittance into the gastrointestinal tract.

7. A sosage form for delivering a benefical drug to an environment of use, wherein the dosage form comprising:
(a) a wall that surrounds and defines an internal compartment;
(b) a dosage amount of an anti-inflammatory drug selected from the group consisting of acylcarboxylic acid and enolic acid anti-inflammatory drug in the compartment;
(c) means for producing gaseous carbon dioxide in the compartment, said means comprising a polymeric film selected from the group consisting of olefin and vinyl polymeric films, condensation polymeric films, addition polymeric films and organo-silicon polymeric films surrounding a member selected from the group consisting of a water soluble carbonate and bicarbonate, which carbonate and bicarbonate are released by the film and effervesces on contact with the acidic drug to produce carobn dioxide; and,
(d) at least one passageway in the wall connecting the compartment with the exterior of the dosage form.

* * * * *

UNITED STATES PATENT AND TRADEMARK OFFICE
CERTIFICATE OF CORRECTION

PATENT NO. : 4,847,093
DATED : Jul. 11, 1989
INVENTOR(S) : Atul D. Ayer and Patrick S.L. Wong It is certified that error appears in the above-indentified patent and that said Letters Patent is hereby corrected as shown below:

Title page, item [21] "Appl. No.: 668,761" should read --876,138--.

Signed and Sealed this

Seventh Day of November, 1995

Attest:

BRUCE LEHMAN

Attesting Officer     Commissioner of Patents and Trademarks